United States Patent [19]

White

[11] Patent Number: 4,513,456
[45] Date of Patent: Apr. 30, 1985

[54] INTRAOCULAR LENS

[76] Inventor: Thomas C. White, 1127 Holly Dr., Sioux Falls, S. Dak. 57105

[21] Appl. No.: 509,420

[22] Filed: Jun. 30, 1983

[51] Int. Cl.³ .......................... A61F 1/16; A61F 1/24
[52] U.S. Cl. ......................................................... 3/13
[58] Field of Search ......................................... 3/13, 1

[56] References Cited

U.S. PATENT DOCUMENTS 4,338,687  7/1982  Rainin ..................................... 3/13
4,403,354  9/1983  Rainin ..................................... 3/13

Primary Examiner—Ronald L. Frinks
Attorney, Agent, or Firm—James R. Haller; Gregory P. Kaihoi

[57] ABSTRACT

An intraocular lens device is described which includes a fixation element in the form of an elongated, resilient strut extending outwardly of the lens for contact with supportive eye structure and thence inwardly toward the lens, the strut having a free end. A second strut also is carried by the lens adjacent the first mentioned strut and provides an open end oriented to receive and immobilize said free end, thereby restraining the latter from substantial movement within the eye.

3 Claims, 8 Drawing Figures

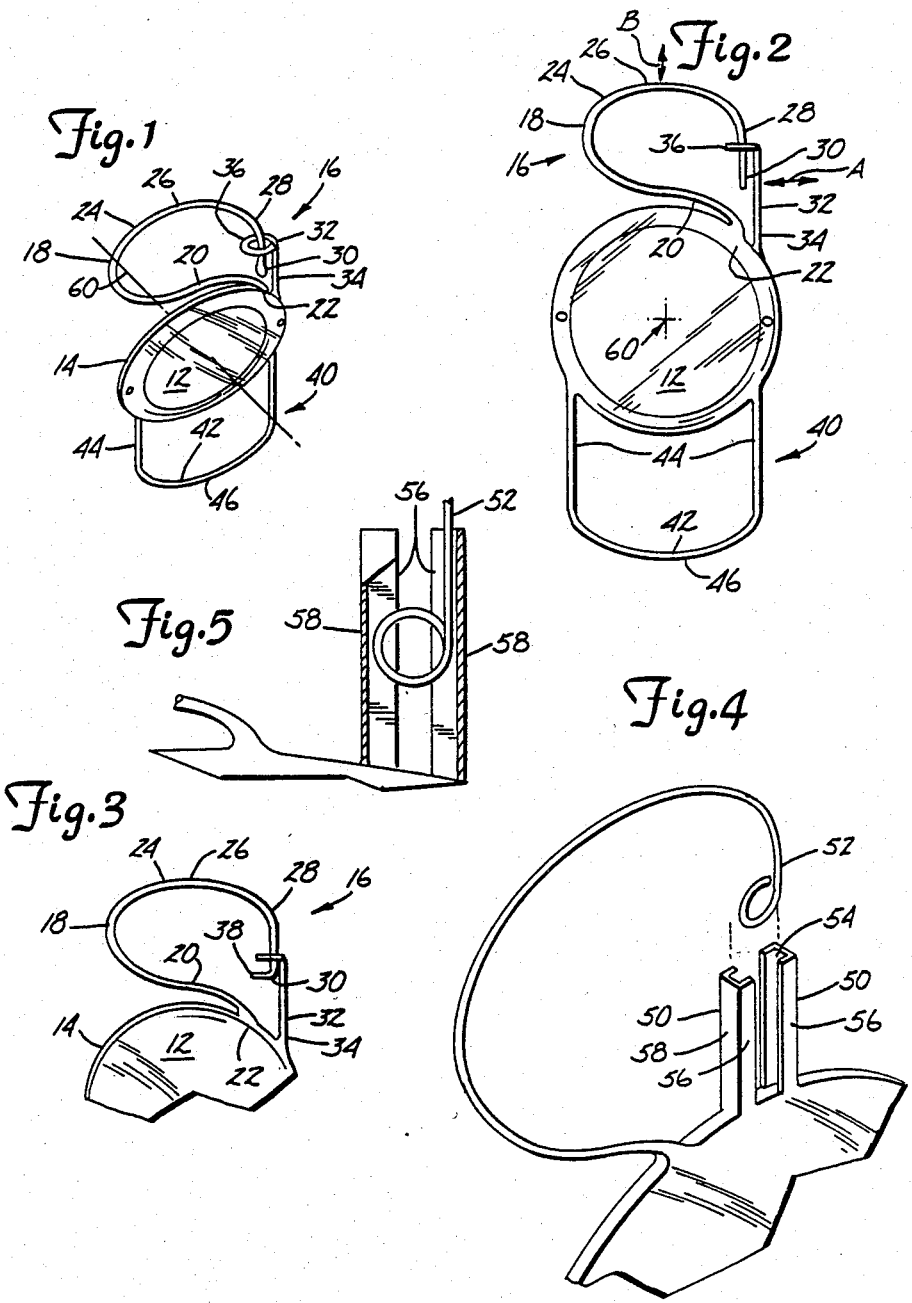

INTRAOCULAR LENS

TECHNICAL FIELD

This invention is in the field of medical prosthesis, and particularly relates to the use of artificial lenses to replace tissue lenses removed during cataract surgery.

BACKGROUND ART

Cataract surgery involves the removal of the lens or lens nucleus from the eye of a patient, and it is common in such procedures to implant within the eye an artificial lens, the lens being supported in either the anterior or posterior chambers and being supported by wires or other structure that extend from the lens outwardly into contact with supportive, circumferential grooves or other structures adjacent the iris.

Typical intraocular lenses are disclosed in the following references:
U.S. Pat. No. 4,092,743 (Kelman)
U.S. Pat. No. 4,174,543 (Kelman)
U.S. Pat. No. 4,261,065 (Tennant)
U.S. Pat. No. 4,328,595 (Sheets)
U.S. Pat. No. 4,338,687 (Rainin)
U.S. Pat. No. 4,340,979 (Kelman)
U.S. Pat. No. 4,343,050 (Kelman)
U.S. Pat. No. 4,370,760 (Kelman)

Intraocular lenses in general are characterized by including a central lens or lenticular portion, and two or more struts, usually radially resilient, that extend outwardly of the lens and which gently but elastically engage appropriate circumferential eye structure adjacent the iris. The struts of intraocular lenses that are to be employed in the anterior chamber of the eye, that is, anterior of the iris, may engage the internal scleral sulcus, commonly called the "angle", formed between the iris and the internal periphery of the cornea, avoiding substantial contact or interference with the trabacular meshwork. Intraocular lenses intended to be mounted in the posterior chamber, that is, posterior of the iris, commonly have struts or other fixation devices that engage the ciliary recess or the circumferential edges of the posterior lens capsule that remains after removal of the lens nucleus.

In normal human eyes, aqueous humor is discharged into the posterior chamber, flows through the pupil into the anterior chamber, and is removed from the anterior chamber by means of (Schlemm's canals or the trabacular meshwork) adjacent the internal schleral sulcus. When the flow of aqueous humor in this manner is restricted or blocked, as when the anterior face of vitreous humor comes into contact with the iris following cataract surgery, acute glaucoma can result. Accordingly, small surgical openings, or peripheral iridectomies, are formed in the iris to provide flow paths for aqueous humor. Such peripheral iridectomies preferably are basal, that is, they are formed desirably at the outer periphery of the iris. Nonbasal peripheral iridectomies, formed in the iris at positions spaced from its periphery, have also been used but are less preferred in that they may become blocked or plugged by the anterior vitreous face.

Intraocular lenses commonly are surgically placed and rotated so that their supporting structure is out of contact with basal peripheral iridectomies, and it generally is expected that the intraocular lenses will remain permanently in position and will not rotate about the lens axis. Intraocular lenses commonly are formed with small holes or indentations adjacent the lens periphery to permit a surgeon, utilizing specialized instruments, to rotate the lens into the desired position spaced from the iris openings formed through basal peripheral iridectomy procedures.

Unfortunately, it has now been observed that intraocular lenses may not remain permanently fixed against rotation with respect to the lens axis. The lenses may in fact be rotationally displaced through commonplace rubbing of the eyes, with the result that the lens fixation elements over a period of months or years may come into contact with and may actually enter the basal peripheral iridectomies formed during the lens implantation surgery. Inflammation of the iris (iritis) may result from such iris capture, but more importantly, the lens itself, due to the resulting loss of placement of its fixation elements, may tilt or may become dislocated with respect to the pupillary axis. As a result, the lens, if implanted in the anterior chamber, may touch and cause severe damage to the inner corneal surface or if placed in the posterior chamber, may cause rupture of the anterior vitreous face causing vitreous prolapse into the iridectomy wound, in turn leading to cystoid macular (retinal) edema. The rotation of intraocular lenses in this manner and the resulting problems that arise have only recently been recognized. Unfortunately, such problems often arise only months or years after a lens has been implanted and routine consultation with a surgeon has been terminated. As a result, severe damage to the eye can readily occur before corrective surgical steps can be taken.

Certain of the fixation elements previously employed with intraocular lenses are of a wire or of a springy, wire-like material formed into generally "U"-shaped loops with each end of each loop being fixed to the lens. To the extent that the loops are smoothly curved, protrusion of the loops into or through an iridectomy opening may be avoided; however, because of the fixation of such loops at both ends to the lens, the loops provide only limited resilience. A lens with the semi-rigid loops accordingly is difficult to insert and properly place within the eye, since the loops are elastically deformed only with some difficulty. It has been proposed in U.S. Pat. No. 4,338,687 to provide the lens itself with internal springs which resiliently receive ends of the "U"-shaped loops to enable the loops as a whole to be elastically moved toward and away from the lens periphery. The lens structure, however, is heavy, complicated and expensive.

DISCLOSURE OF INVENTION

In one embodiment, the intraocular lens device of the invention comprises a lens for placement adjacent the side of the iris of an eye, the lens having an axis substantially alignable with the pupillary axis. Fixation elements are carried by the lens for supportive engagement with eye structure circumferential of the pupillary axis. At least one fixation element comprises an elongated, resilient strut having a proximal portion carried by the lens, a medial portion having a contact surface engageable with circumferential eye structure, and a distal portion extending inwardly from the medial portion toward the lens and having a free end to permit the contact surface to move elastically toward and away from the lens. Free end capture means is carried by the lens and defines an opening oriented to receive the free end of the strut to prevent iris capture of the free strut end and restrain the latter from movement parallel to the lens axis within the eye. To accommodate limited side-to-side movement of the free end in the plane of the strut, the capture means desirably is resiliently mounted to permit resilient movement of the opening thereof in the same direction. Desirably, the free-end capture means comprises a second resilient strut or protrusion extending from the lens and having a loop at its end to receive the free end of the first-mentioned strut. The free strut end may include contact means for contacting the capture means and preventing or restraining escape of the free end therefrom.

During surgical placement of the lens device in a human eye, the contact surface may flex readily and elastically to permit proper installation and to bear outwardly against the supportive circumferential eye structure, and the resulting movement of the free end is accommodated by the capture means. The free end is prevented by the capture means from entering and damaging adjacent eye structure or from entering an iridectomy opening.

BRIEF DESCRIPTION OF DRAWINGS

FIG. 1 is a perspective view of the lens device of the invention;

FIG. 2 is a plan view of the device shown in FIG. 1;

FIG. 3 is a broken-away plan view of a device similar to that of FIG. 2 but showing a modification of the invention;

FIG. 4 is a broken-away, perspective view showing another modification of the invention with one element thereof removed from another element for purposes of clarity;

FIG. 5 is a broken-away, cross-sectional view of the device of FIG. 4;

BEST MODE FOR CARRYING OUT THE INVENTION

Figure 6:
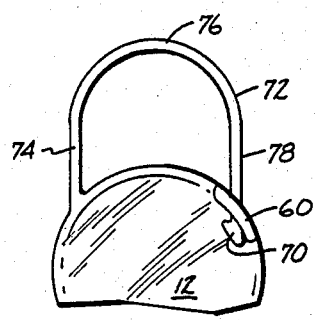
FIG. 6 is a broken-away, plan view of a further modification.

Referring first to FIG. 1, a lens of polymethylmethacrylate or other suitable transparent material is shown as (12). Arising from the periphery (14) of the lens is a fixation element shown generally as (16), this element comprising an elongated resilient strut (18) having a proximal portion (20) attached at one end to the lens (at 22), a medial portion (24) having an outer contact surface (26) contactable with eye structure circumferentially of the pupillary axis of an eye, and a distal portion (28) extending generally toward the lens and terminating in a free end (30). Although the strut (18) may be formed generally in the shape of a "U" with one end carried by the lens and the other end terminating short of the lens, the embodiment shown in FIGS. 1-3 is preferred in which the proximal portion (20) of the strut is provided with a gentle curve spiraling away from the periphery (14) of the disc and in which the medial portion is curved in the opposite direction to provide a gently rounded outer contact surface (26), the strut having a configuration similar to a bass clef.

A second strut is shown at (32) and, in the embodiment of FIGS. 1-3, includes a resilient shaft portion (34) extending outwardly of the lens and terminating in a loop (36) typifying free end capture means and that is open outwardly and positioned to receive the free end (30) of the strut (18). The shaft (34) preferably is resilient so that it may flex from side to side as shown by the arrows A in FIG. 2. The flexible strut (18) enables the outer, eye structure-contacting surface (26) to move elastically inwardly and outwardly of the lens as shown by the arrows B in FIG. 2; such elastic movement results largely from the elastic nature of the proximal portion (20) of the strut (18) coupled with the freedom of motion of the free end, and results in some side-to-side movement of the length of the strut (18) adjacent its end (30) as shown by arrows B in FIG. 2. Such movement is accordingly accommodated by the back and forth movement permitted the second strut (32), thereby permitting the entire fixation element (16) to flex under radial pressure provided by contact of eye structure with the contact surface (26).

If desired, the end (30) of the strut (18) may be provided with a bent-over end portion (38) (FIG. 3) typifying contact means and restraining the strut (18) from escaping from the strut (32).

Although desirably two or more fixation elements identical to that depicted at (16) in the drawings are employed, other fixation elements also may be employed, and the embodiment of FIGS. 1 and 2 show a second fixation element (40) in diametric opposition to the element (16), the element (40) being generally "U"-shaped and being attached at its ends to the periphery (14) of the lens. Although some resilient movement is provided the strut (40), as by flattening of its central portion (42) and outward flexing of its legs (44), generally the radial resiliency provided by the element (40) is substantially less than that afforded by the element (16). The central portion (42) of the element (40) includes an outer surface (46) engageable with supportive circumferential eye structure.

In the embodiment of FIGS. 4 and 5, the free end capture means is depicted as being formed of a pair of generally C-shaped channels (50), the openings of the channels confronting one another to define a pair of spaced, confronting slots within which may be received the end (52) of a resilient strut similar to the strut (16) described above. The end (52) of the strut preferably is looped or otherwise provided with a shape readily and slidably receivable within the confronting slots (54) of the channels (50), the side walls (56) of the channels and their end walls (58) generally limiting movement of the end (52) of the strut to directions inwardly and outwardly of the channels.

In use, following surgical removal of the natural lens or lens nucleus from a human eye through a surgical incision in the cornea adjacent the limbus, a device of the invention may be inserted through the incision and delicately moved into place with the contact surfaces (26), (46) in resilient contact with supporting, circumferential eye structure. As is well known, when intraocular lenses are to be supported within the anterior chamber of the eye, the contact surfaces (26), (46) are placed within and in contact with the internal scleral sulcus, the fixation elements being slightly displaced from the plane of the lens so as to space or vault the lens anteriorly within the anterior chamber with the lens being supported between and spaced from the corneal endothelium and the iris. When placed in the posterior chamber, the contact surfaces (46), (26) may be positioned against and within the ciliary recess, or within the rims of the remaining posterior lens capsule when only the nucleus of the lens has been removed. When used as a posterior intraocular lens, the device of the invention preferably spaces or vaults the lens posteriorly within the posterior chamber, spacing the same from the posterior surfaces of the iris.

Referring again to the embodiments of FIGS. 1 and 2, when the lens device has been suitably implanted within an eye, the contact surfaces (26), (46) bear radially outwardly against the supportive eye structure, there being sufficient contact between these surfaces and the supportive eye structure as to prevent the lens from turning or twisting within the eye. It is understood that the lens size is so chosen as to permit the lens to be implanted with the lens axis (60) generally aligned with the pupillary axis of the eye. The free end (30) of the strut (18) protrudes a sufficient distance through the capture means (typified in FIGS. 1 and 2 as loop (36)) as to enable the strut (18) to resiliently expand outwardly into contact with the supportive eye structure and yet retain the free end (30) within the loop (36). Similarly, in the embodiment of FIGS. 4 and 5, the end of the strut (52) extends for a sufficient distance within the channels (50) as to permit the strut to expand and yet maintain its free end captured within the channels.

The capture of the free end, as typified at (30) in FIGS. 1-3, largely immobilizes the free end once the lens device has been positioned within the eye and prevents the free end from moving into damaging contact with adjacent eye tissue such as the iris. Particularly, the free end of the strut (18) is prevented from being captured by basal or nonbasal peripheral iridectomy openings formed in the iris. Although substantially immobilized within the loop (36), the strut (18) may yet be flexed generally radially inwardly and outwardly of the lens within limits, as when an eye is rubbed by a patient, without permitting escape of the free end (30) of the strut from the loop (36). Preferably, the strut (18) is so formed that the free end (30) thereof, when the strut is in its relaxed or rest position, remains within the loop (36) (or, with reference to FIGS. 4 and 5, within the channels (50)). In this manner, even though the lens were to become dislodged within the eye, the free end of the flexible strut tends to remain protectively captured by the free end capture means. As mentioned above, the free end may be provided with an enlarged contact portion, typified by the bent-over portion (38) in FIG. 3, to structurally prevent the free end from escaping from the capture means.

Figure 7:
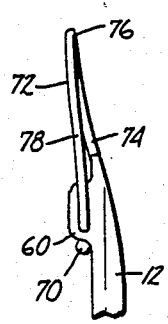
FIG. 7 is a side view, broken-away, of the device of FIG. 6.
Figure 8:
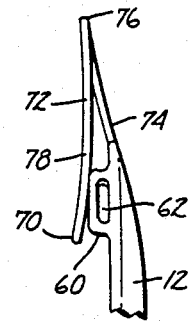
FIG. 8 is a view similar to FIG. 7 but showing one element of the device removed from another for purposes of clarity.

FIGS. 6-8 show a particularly preferred embodiment utilizing a free end capture means comprising a protrusion (60) formed at the lens periphery and extending generally parallel to the lens axis. An aperture (62) formed in the protrusion (60) is open outwardly and is oriented to capture the free end (70) of the strut (72), as shown in FIGS. 6 and 7. As in the previously described embodiments, the strut (72) includes a proximal portion (74) attached at one end to the lens periphery, a medial portion (76) having an outer, eye-structure contact surface, and a distal portion (78) terminating in the free end (70). The latter may have an enlarged or barbed end as shown in FIG. 6 to enable it to be readily inserted but not easily withdrawn from the aperture (62). FIG. 8 shows the device as it may be molded or otherwise fabricated and before the free end (70) is inserted in the aperture (62).

The lens device of the invention may be fabricated by known techniques, and may be substantially completely molded as an integral unit. The loop (36) in the embodiment of FIGS. 1-3 may require additional machining or heat bending. Also, the flexible strut (18) may be initially molded in a plane angled slightly to the plane of the lens for subsequent insertion of its free end within the loop (36) (or within the channels (5) shown in FIGS. 4 and 5). Alternatively, the fixation elements may be separately attached to the lens. The lens desirably is of a transparent, biologically generally inert material such as poly (methyl methacrylate), and the fixation elements may be formed from the same material or from polyethylene or other suitable material. If desired, the fixation elements may be formed of a resilient metal wire. The fixation elements may be attached to the periphery of the lens, as shown in the drawing, or may be appropriately attached to one or both of the lens surfaces.

While a preferred embodiment of the present invention has been described, it should be understood that various changes, adaptations and modifications may be made therein without departing from the spirit of the invention and the scope of the appended claims.

What is claimed is:

1. An intraocular lens device comprising:
   (a) a lens for placement adjacent the side of the iris of an eye with its axis substantially aligned with the pupillary axis;
   (b) fixation elements carried by the lens for supportive engagement with eye structure circumferential of the pupillary axis of the eye, at least one fixation element comprising an elongated resilient strut having a proximal portion carried by the lens, a medial portion having a contact surface engageable with said eye structure, and a distal portion extending inwardly from the medial portion toward the lens and having a free end to permit the contact surface to move elastically toward and away from the lens; and
   (c) free end capture means comprising a second strut extending from the lens and having a loop at its outer end oriented to protectably receive the free end of the strut.

2. An intraocular lens device comprising:
   (a) a lens for placement adjacent the side of the iris of an eye with its axis substantially aligned with the pupillary axis;
   (b) fixation elements carried by the lens for supportive engagement with eye structure circumferential of the pupillary axis of the eye, at least one fixation element comprising an elongated resilient strut having a proximal portion carried by the lens, a medial portion having a contact surface engageable with said eye structure, and a distal portion extending inwardly from the medial portion toward the lens and having a free end to permit the contact surface to move elastically toward and away from the lens; and
   (c) free end capture means comprising a protrusion extending from the lens periphery generally parallel to the lens axis and having an aperture therein spaced from the plane of the lens and oriented to protectably receive the free end of the strut.

3. The intraocular lens of claim 2 in which the free strut end is barbed for easy insertion into but difficult removal from said aperture.

* * * * *